United States Patent
Hakkala

(10) Patent No.: US 8,171,589 B2
(45) Date of Patent: May 8, 2012

(54) INDIVIDUALLY FORMED FOOTWEAR AND A RELATED METHOD

(75) Inventor: Erkki Hakkala, Helsinki (FI)

(73) Assignee: Footbalance System Oy, Helsinki (FI)

( * ) Notice: Subject to any disclaimer, the term of this patent is extended or adjusted under 35 U.S.C. 154(b) by 127 days.

(21) Appl. No.: 12/849,953

(22) Filed: Aug. 4, 2010

(65) Prior Publication Data

US 2010/0293727 A1 Nov. 25, 2010

Related U.S. Application Data

(62) Division of application No. 11/486,080, filed on Jul. 14, 2006, now Pat. No. 7,793,433.

(51) Int. Cl.
*A43D 1/00* (2006.01)

(52) U.S. Cl. .................... 12/146 B; 12/146 M

(58) Field of Classification Search ............. 12/146 B, 12/146 M, 142 N; 36/93, 44, 43, 154, 153, 36/88

See application file for complete search history.

(56) References Cited

U.S. PATENT DOCUMENTS

| | | | |
|---|---|---|---|
| 4,139,337 A | 2/1979 | David et al. | |
| 4,669,142 A | 6/1987 | Meyer | |
| 4,674,206 A * | 6/1987 | Lyden | 36/88 |
| 4,716,662 A | 1/1988 | Bar | |
| 5,025,476 A | 6/1991 | Gould et al. | |
| 5,042,100 A * | 8/1991 | Bar et al. | 12/142 N |
| 5,083,910 A | 1/1992 | Abshire et al. | |
| 5,095,570 A * | 3/1992 | Bar et al. | 12/142 N |
| 5,101,580 A * | 4/1992 | Lyden | 36/93 |
| 5,203,793 A | 4/1993 | Lyden | |
| 5,555,584 A * | 9/1996 | Moore et al. | 12/142 N |
| 5,632,057 A * | 5/1997 | Lyden | 12/146 B |
| 5,722,186 A | 3/1998 | Brown | |
| 5,733,647 A | 3/1998 | Moore, III et al. | |
| 5,829,171 A | 11/1998 | Weber et al. | |
| 5,891,545 A | 4/1999 | Delude | |
| 6,598,319 B2 | 7/2003 | Hardt | |
| 2005/0044751 A1 | 3/2005 | Alaimo | |
| 2006/0086004 A1 | 4/2006 | Davis et al. | |

FOREIGN PATENT DOCUMENTS

| | | |
|---|---|---|
| ES | 2120860 A1 | 11/1998 |
| JP | 10099103 A | 4/1998 |
| WO | 90/05345 A1 | 5/1990 |
| WO | 91/07152 A | 5/1991 |
| WO | 91/12740 A | 9/1991 |
| WO | 03/037124 A | 5/2003 |
| WO | 2005044105 A1 | 5/2005 |

OTHER PUBLICATIONS

International Search Report dated Jun. 26, 2007 corresponding to PCT/FI2006/000254.
International Search Report dated Oct. 12, 2007 corresponding to PCT/FI2007/050366.
Search Report dated Jul. 19, 2007 corresponding to Finnish Application 20065708.
Translation of Japanese Office Action, application No. 2009-520001, dated Dec. 20, 2011.

* cited by examiner

*Primary Examiner* — Ted Kavanaugh
(74) *Attorney, Agent, or Firm* — Young & Thompson

(57) ABSTRACT

Individually formed footwear such as shoes and insoles for correcting the feet position and alleviate related problems. The shoe or insole includes at least one layer made of thermoplastic material, which material is advantageously chosen from a group of ABS, PVC, A-PET and PETG. A method for providing such footwear to a client at a retail store is likewise presented.

6 Claims, 5 Drawing Sheets

INDIVIDUALLY FORMED FOOTWEAR AND A RELATED METHOD

CROSS REFERENCE TO RELATED APPLICATIONS

This application is a divisional of application Ser. No. 11/486,080 filed on Jul. 14, 2006. The entire contents of each of the above-identified applications are hereby incorporated by reference.

FIELD OF THE INVENTION

The current invention generally relates to footwear. In particular the invention concerns personalized shoes, insoles and a method for obtaining those.

BACKGROUND OF THE INVENTION

Approximately 70% of the world population suffer from some sort of foot problems. Only few of the total number have had a chance to purchase insoles that alleviate at least part of the problems. Traditionally, custom-made shoes and insoles have been manufactured by professional shoemakers, physiotherapists, or podiatrists. So far the associated purchase process has been rather time-consuming and costly; a person willing to spend 120-250 EUR on custom made insoles or more than 300 EUR in bespoke shoes has to visit one of aforesaid professionals or their remote partner to get their feet characteristics measured including e.g. a foot size and other properties, advantageously also problem-causing features, after which the order is placed in a waiting list for initiating the actual manufacturing process by the professional. Often the delay between placing the order and receiving the customized shoes/insoles thus extends to few days or even few weeks, which makes the overall process rather awkward especially from a standpoint of a casual client.

Foot motion/gait problems reflect to soles, ankles, knees, hips, back, etc; that is why their treatment and prevention is particularly beneficial to the whole human well-being. An individual takes around 15 000-16 000 steps every day. The load on feet in sports is many times the weight of the body. For example, the ground force is about three times one's body weight while running and 7.5 times while playing basketball due to jumps and other irregular moves. Provided that the foot position is correct, the load divides evenly between the upper joints.

A common condition called pronation refers to inward (i.e. medial) roll of the foot (especially heel and arch), which turns into overpronation when the foot rolls too much. In contrast, oversupination is caused by too small inward roll. Both conditions easily cause pain, wear and even stress injuries in the feet and various body joints.

Different (arch) support insoles are available for correcting the foot position. They have been designed to support longitudinal medial and lateral arch but without separately glued wedges they do not actually correct foot position. Wedging is a time-consuming and expensive process. The obtained result depends on the person doing the task and still tends to be rather inaccurate. As another drawback, after gluing the wedges to the soles one cannot take a new mold without first removing the wedges.

Ready-made supports in the insoles do not provide a perfect match to anyone's feet, as people do not generally bear identical feet shape. Accordingly, many support insoles are ultimately deemed inconvenient due to their lousy fit.

SUMMARY OF THE INVENTION

In order to alleviate aforesaid problems the current invention provides, as its one aspect, an insole for a shoe, which insole comprises at least one layer made of thermoplastic material, which material is chosen from a group consisting of: ABS, PVC, A-PET, and PETG so that the selected material becomes plastic substantially under 95° C. and above 45° C., i.e. somewhere within the range.

In another aspect a shoe comprises a sole having at least two layers one of which being made of thermoplastic material.

An insole or a shoe that is to be subjected to a shaping (or actually reshaping as it inherently has some kind of basic form after manufacturing) procedure of the invention for correcting the foot position is hereinafter called a preform.

In a further aspect a method of producing an individually formed insole includes:
  choosing one or more, e.g. a pair of, insole preforms from a selection of preforms having a thermoplastic layer,
  heating the chosen preform above the glass transition temperature (Tg) temperature of the thermoplastic layer in case the preform lacks preheating,
  guiding a client to step on the heated preform,
  adjusting the angle of the ankle to the right position with help and guidance of an orthopedic or other trained person,
  adjusting the client's foot so that the plantar arch settles to a normal high position, and
  waiting for the temperature of the heated insole preform to drop under the glass transition temperature of the thermoplastic.

Yet in a further aspect a method of producing an individually formed shoe includes the following steps:
  choosing one or more, e.g. a pair of, shoe preforms from a selection of shoe preforms,
  heating the chosen shoe preform above the glass transition temperature of the thermoplastic layer of the shoe preform in case the preform lacks preheating,
  guiding the client to step into the heated shoe preform,
  adjusting the client's foot so that the plantar arch settles to a normal high position,
  adjusting the angle of the ankle to the right position with help and guidance of an orthopedic or other trained person,
  taking the shoe preform off from the foot, and
  waiting for the temperature of the shoe preform to drop under the glass transition temperature of the thermoplastic.

Still in a further aspect a method for providing individually formed footwear to a client comprises:
  arranging a sales spot including a plurality of alternative articles selected from the group consisting of: an insole, a liner for a shoe, and a shoe; said sales spot further including means for customising an article belonging to said plurality of articles to the client's foot,
  studying a foot of the client so as to enable choosing an article belonging to said plurality of articles,
  treating, preferably heating by said means for customizing, at least part of the chosen article to render its form responsive to an external force introduced thereon,
  placing the client's foot in contact with the treated article in accordance with the predetermined use thereof, and
  manually shaping the treated article so as to correct the foot position by conforming thereto.

The utility of the invention arises from a number of issues. First, the individually formed shoe or insole provides natural arch support and divides the ground force more evenly through the foot, knee, hip, and the back. Secondly, it reduces overpronation or oversupination and realigns the gait. This affects positively to the body posture and alleviates fatigue, sprained ankles, rubbing and pain. The invention further stabilizes the foot, adds lateral support of the foot and strengthens it to reduce loss in muscle power. Yet, the transverse arch is supported when the thermoplastic layer extends under it.

Further, when considering the issue from a retail perspective, the shoes/insoles can be offered through common retail stores, e.g. sport or shoe stores, and the required customisation process by a trained sales clerk takes only minutes. The sales spot consumes only a minor space (few square meters) and compulsory investments in equipment can be kept low. Provision of customized insoles cultivates the pro image emanating from the retailer and offers a promotional value in relation to other products as well; it attracts people to visit the store and raises the sales figures of related products (shoes/insoles, socks, etc) respectively. The profit margin can be kept high while the retail price is still considerably lower than with its prior art antecessors.

In an embodiment of the invention an insole or a shoe has a thermoplastic layer that extends substantially over the major area of the insole, optionally still leaving at least the border areas intact for facilitating easy adjustment and cutting thereof.

In another embodiment of the invention an insole or a shoe has a thermoplastic layer that covers laterally only part of the insole/shoe. Advantageously the thermoplastic still reaches out lengthwise at least from under the heel to under the plantar arch and in lateral direction almost to the whole width of the insole.

BRIEF DESCRIPTION OF THE DRAWINGS

In the following, the invention is described in more detail by reference to the attached drawings, wherein.

DETAILED DESCRIPTION OF THE EXEMPLARY EMBODIMENTS

A preform (~blanket) insole has at least one layer, which is made of thermoplastic and reaches out at least from under the heel to under the plantar arch of the target person's, hereinafter client, foot. Advantageously two or three material layers that are connected together are used in the preform insole for the comfort of the client. The upper layer (if used) of the preform insole is placed against the foot and the lower layer is placed against the shoe. Materials of these two layers can be selected among any prior art materials used in insoles. For example, the lower layer may be constructed from a known material such as Rheluflex (trademark of Rhenoflex GmbH Ltd) comprising non-woven polyester as a carrier, ionomer-resin-ethylvinylacetate blend as an extruded core, and EVA-Hotmelt as an adhesive.

The middle layer of the insole (in case of three layers) is made of thermoplastic. The used thermoplastic can be selected from a large group of known thermoplastics. The critical value is the temperature, so-called glass transition temperature, where the thermoplastic becomes plastic and on the other hand turns back to solid form when the temperature is decreasing after shaping the insole. This temperature should not generally be so high that the insole feels uncomfortable against the client's foot. Notwithstanding a high glass transition temperature, a thermoplastic is still applicable if it can be cooled down enough prior to placing in contact with the foot provided that the thermoplastic remains plastic, i.e. mouldable. Adequate temperature for the thermoplastic to become plastic is preferably somewhere under 95° C. and above 45° C. Advantageously the range is from 50° C. to 85° C. Suitable materials that become or are plastic within the preferred ranges are for example thermoplastic polyesters A-PET (Amorphous polyester terephthalate) and PETG (glycol-modified polyethylene terephthalate, which is a copolyester), or such with essentially similar characteristics. Also e.g. ABS (acrylonitrile butadiene styrene), PVC (polyvinyl chloride) can be used.

Thickness of the thermoplastic layer shall be preferably selected so as to provide reasonable support to the client's foot when the layer is in a rigid state. The thickness may also vary throughout the layer, if e.g. more flexibility is desired under the toe area (thinner) than the plantar arch area (thicker).

Other characteristic required for the thermoplastic dictates that it should be rigid under the melting temperature.

Figure 1:
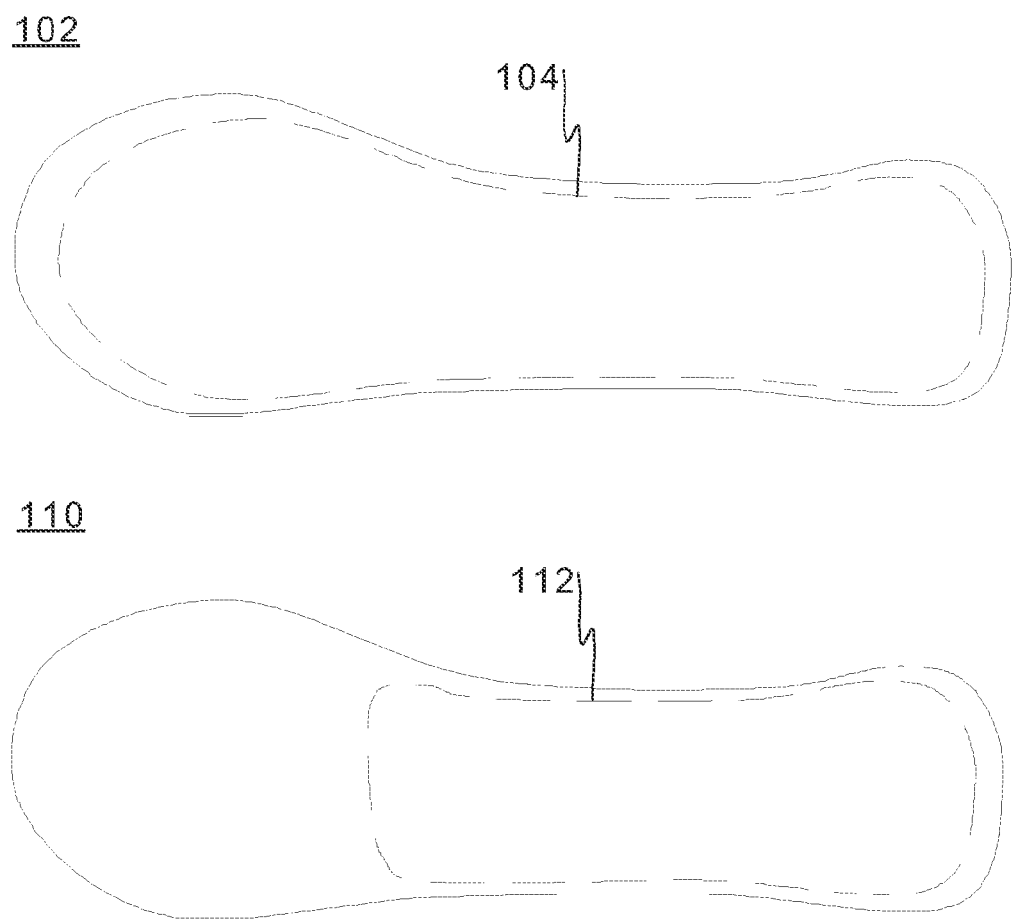
FIG. 1 is a sketch of two insole embodiments according to the invention.

With reference to an embodiment shown in the upper sketch 102 of FIG. 1, the middle layer 104 (or the only layer) made of thermoplastic can cover laterally the whole area of the insole. In alternative embodiment, see sketch 110, the layer 112 covers laterally only a part of the insole. In that option it is necessary that the thermoplastic reaches out lengthwise at least under the heel to under the plantar arch and in lateral direction advantageously almost to the whole width of the insole. As one feasible implementation, the thermoplastic layer is designed so as to reach out from under the heel to the metatarsophalangeal joint of the foot so that transverse arch can be supported. Also, a precut pad can be placed under the transverse arch when the insole is shaped to lift the transverse arch into the optimum position. However, it is advantageous to keep some range at the edge of the insole without the hard thermoplastic in case there is need for little adjustment when the insole is placed in the shoe. Also, the toe area of the insole should remain without the hard thermoplastic to enable natural movement of the foot during walking or running.

One major aspect of the invention relates to producing a preform of an insole that is ready in one piece (thus possibly having separate layers that are connected together with adhesive or such) and easy to heat over the glass transition temperature of the included thermoplastic. After cooling the insole is preferably rigid one-piece structure that corrects the foot position and supports the foot, especially the plantar arch and transverse arch thereof. The plantar arch can be adjusted to a proper high position by pulling the client's toe up and/or by lifting his/her heel up while keeping the toes against a support surface (Windlass effect). The adjustments can be carried out on a soft pad with or without further manual guiding. Alternatively, a trained person may reach a decent result just by hands without a supporting surface.

Alternatively, in accordance with the current invention a shoe can be provided, said shoe having a sole, which can be shaped according to client's foot for correcting the incorrect position thereof. The shoe in this case shall have at least one material layer of thermoplastic. The shoe is advantageously manufactured to include all necessary layers and is just personalized upon purchase. Suitable shoes include, for example, various types of walking shoes, sport shoes, boots, sandals and soft gym shoes.

The sole is advantageously at least a two-piece structure including a thermoplastic layer either situated on top of the sole material or being integrated, for example embedded, within it. The one or more sole layers excluding the thermoplastic layer may comprise e.g. EVA (ethylvinylacetate) or other prior art materials; e.g. aforesaid EVA is even available in different hardnesses. If there is more than one layer the thermoplastic layer can be smaller in lateral direction than the whole sole. It is essential that the thermoplastic layer reaches out at least from under the heel to under the plantar arch of the foot the same way as with the insole. The thermoplastic materials can be selected the same way as with the insole. It may be advantageous to make at least the outer surface of the sole of some wear resistant and good friction characteristics-having material. Optionally, e.g. viscoelastic foam or other material, which may also be thermosensitive, can be used within the shoe, whereby the shoe internals also reshape in addition to mere insole and provide additional comfort/support. With this embodiment can be assured very comfortable personalised shoe that supports tightly the bone structure of the feet and ankle. This is very important if the client has a for example diabetes or rheumatism and the shoe shouldn't cause any friction or abnormal pressure to the foot.

In a further alternative, footwear such as shoes (walking, sports, discipline-specific, etc), skates, ski boots, etc can be offered with preinstalled insoles in accordance with the invention, which insoles shall be then personalized before use. The layers inside the shoe that receive the insole of the invention shall advantageously conform to the insole shapes. Optionally, e.g. viscoelastic foam or other material that is optionally thermosensitive can be used within the shoe, whereby the shoe internals also reshape in addition to mere insole.

Figure 2:
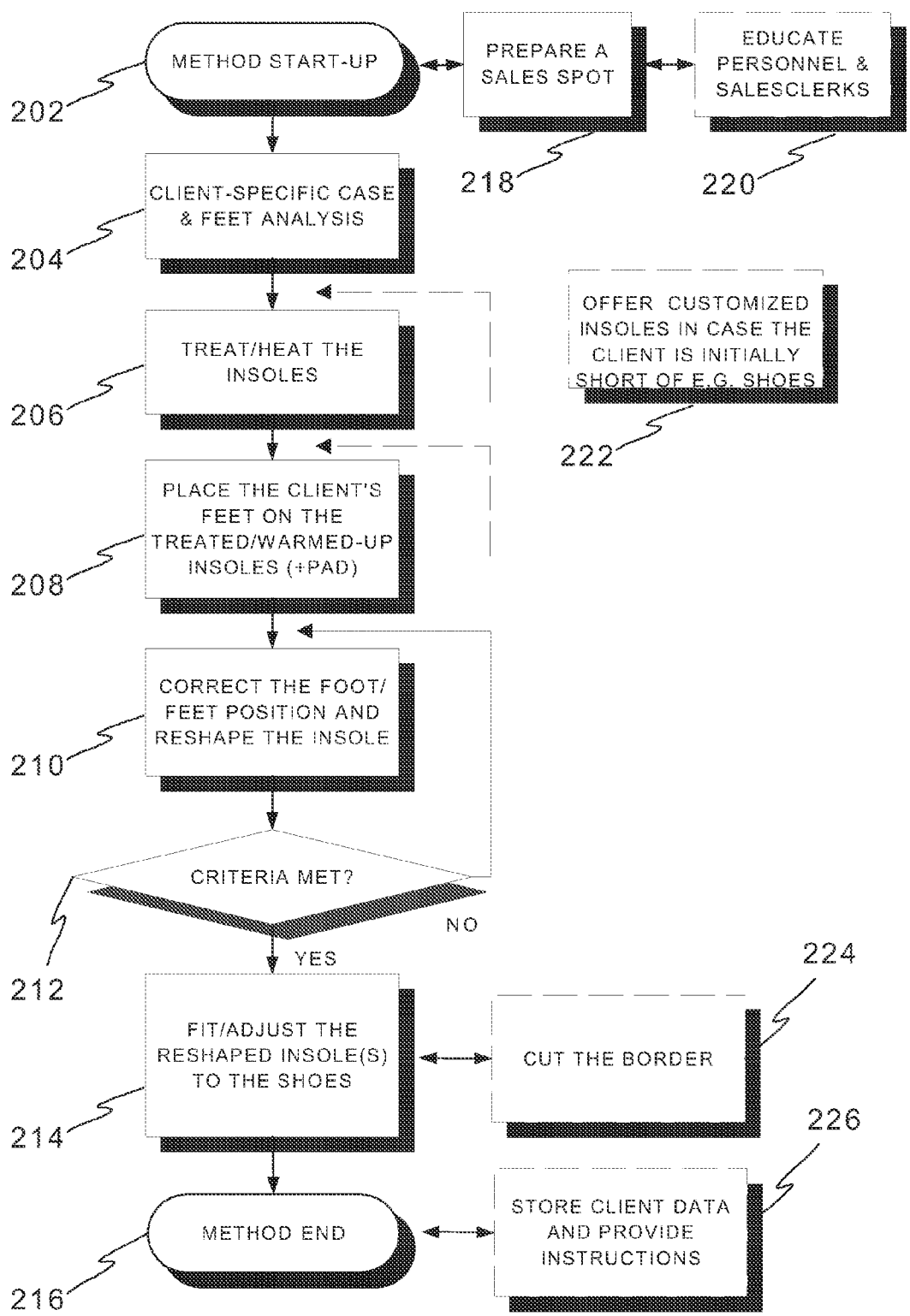
FIG. 2 is a flow diagram representing one example of a method of the invention wherein individually formed footwear is provided to a client.

FIG. 2 discloses a flow diagram, by way of example only, of the method for providing individually formed insoles to a client by a retailer. The insoles may be provided as such or with shoes that may even include the insoles of the invention by default. Likewise, shoes including a mouldable sole of the invention can be offered via the method presented hereinafter. Some of the method steps and associated devices are further visualized in FIGS. 3-5 for clarification.

The inventive concept makes it possible to finalize customised insoles only a few minutes after receiving the assignment. The insoles of the invention can be provided to the retailers as a part of a complete service package including a sales spot, equipment for feet study, and equipment for making customized insoles. The service package may also include training the sales personnel via an educational program that may be an (intensive) course or lection-based.

In step 202, a method start-up, a sales spot is prepared 218 for use at retailer premises. The sales spot may be advantageously delivered as a predetermined ensemble comprising a number of separate elements having a recommended location within the spot so that the spot aggregate can be just conveniently positioned in a preferred location, or alternatively, the retailer may at least partially build it up according to his personal preferences from separate elements if seen useful. The spot includes the necessary means to rapidly provide a customer with properly shaped insoles. Such means may include a stand or a rack with a number of insole preforms (preferably packaged in lightweight, space-saving and at least partially transparent cases, made of e.g. cardboard) with varying properties (size, thickness, basic design, etc), a molding stand with one or more casting pads, a heating system, see numeral 504 of FIG. 5, such as an oven for heating the insole preforms, and basically optional study means for analysing the client's feet and problems/properties thereof in addition to the mere ocular inspection that is anyhow to be performed by the trained staff.

The study means may include, for example, a podoscope, a camera system, and a computer. The podoscope is, by definition, a device for analysing the interaction of the foot and a supporting surface. A client stands on a transparent glass plate of the podoscope, see reference numeral 404 of sketch 402 in FIG. 4, whereupon an image of his feet is shown through a mirror to the person doing the measurements, see lower sketch 410. The study means, e.g. aforesaid podoscope, can also include data acquisition means such as an optical scanner, a camera, or some other suitable apparatus for optically and/or electrically imaging the client's feet and their position (errors), see numeral 406. Such imaging technology enables storing client-dependent data at the retailer for future use and archiving purposes.

Figure 5:
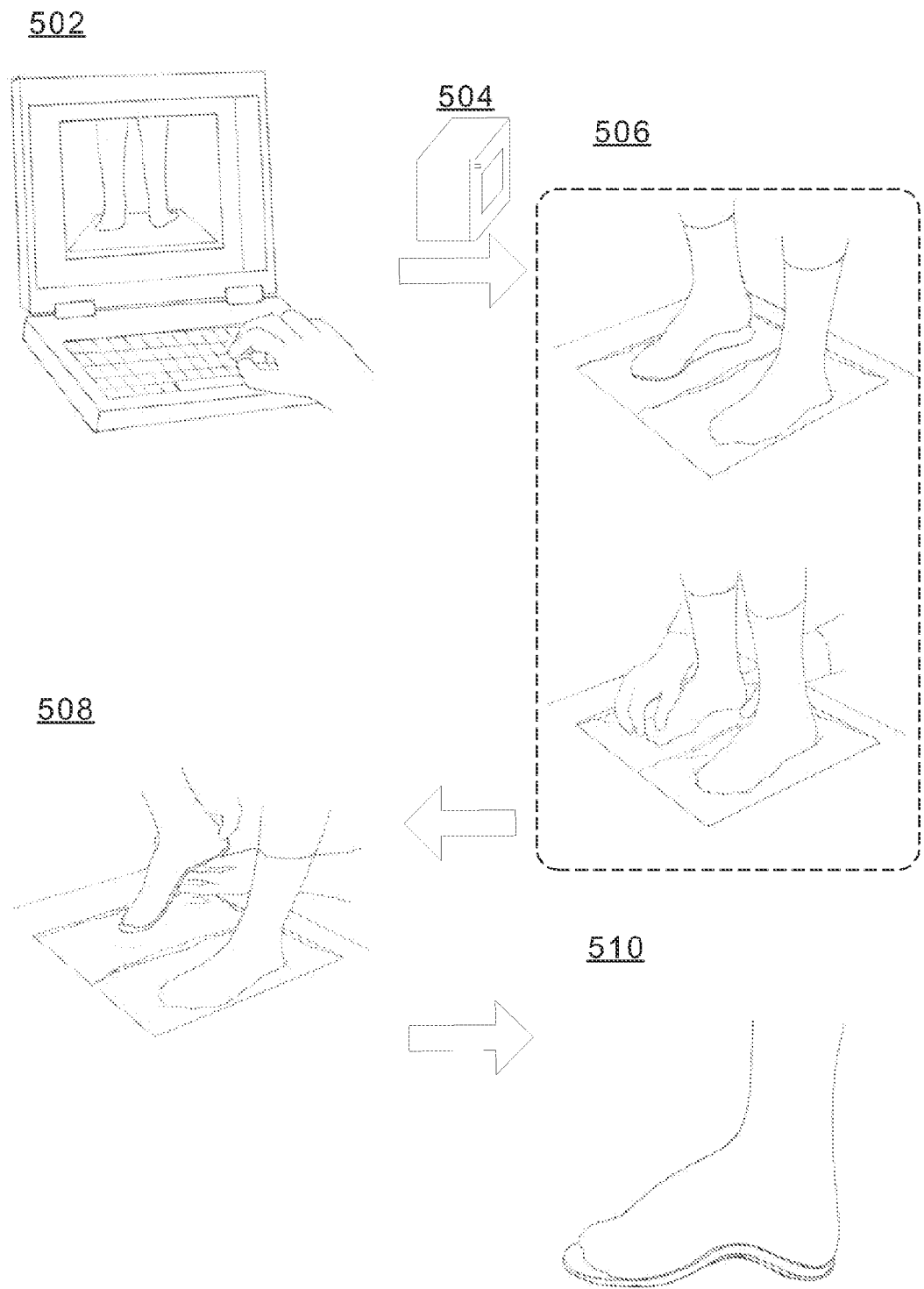
FIG. 5 further visualizes selected method steps of FIG. 2.

The imaging technology may be hooked up to a printer and/or a computer, see numeral 502 of FIG. 5, which is configured to visualize different views, e.g. foot images with optional zooming, silhouettes, etc, on a display based on the gathered data. The trained sales clerk may then point out to the client, via the visualized image, the problems found in his feet position and explain how the situation can actually be improved by the custom-made insoles in accordance with the invention. The computer may also be configured to store the data, preferably client-specifically. Respectively, printed images can be stored. Further, either the computer may include a data transfer interface of its own, e.g. a network interface, or a separate data transfer interface may be coupled thereto or directly to the data acquisition means to transfer the acquired data to external destinations such as the retailer chain's central server or third parties' databases, if allowed by the client.

Yet, the start-up phase includes educating 220 the sales clerks and other personnel about the sales and customisation processes of the insoles of the invention. Preferably, professionals authorized by the insole manufacture shall take care of the training. It is beneficial to the result that the personnel know how to utilize the different insole designs, the oven, the study means, and the molding stand. Certainly, a responsibility for different devices can also be divided between several persons, i.e. one person may take care of the feet analysis whereas the other actually molds the insole to a proper form. Only qualified in-store professionals may be entitled to wear a brand label associated with the insoles. The educational program may include regular follow-ups that can be correspondingly made mandatory for continued qualification and right to wear the brand label.

Reverting to the execution-time flow of the invention, step 204 refers to a client-specific analysis phase during which a trained sales clerk initially studies the client's needs either by manual/ocular investigation of the feet or by listening to the client, preferably by doing both.

Figure 3:
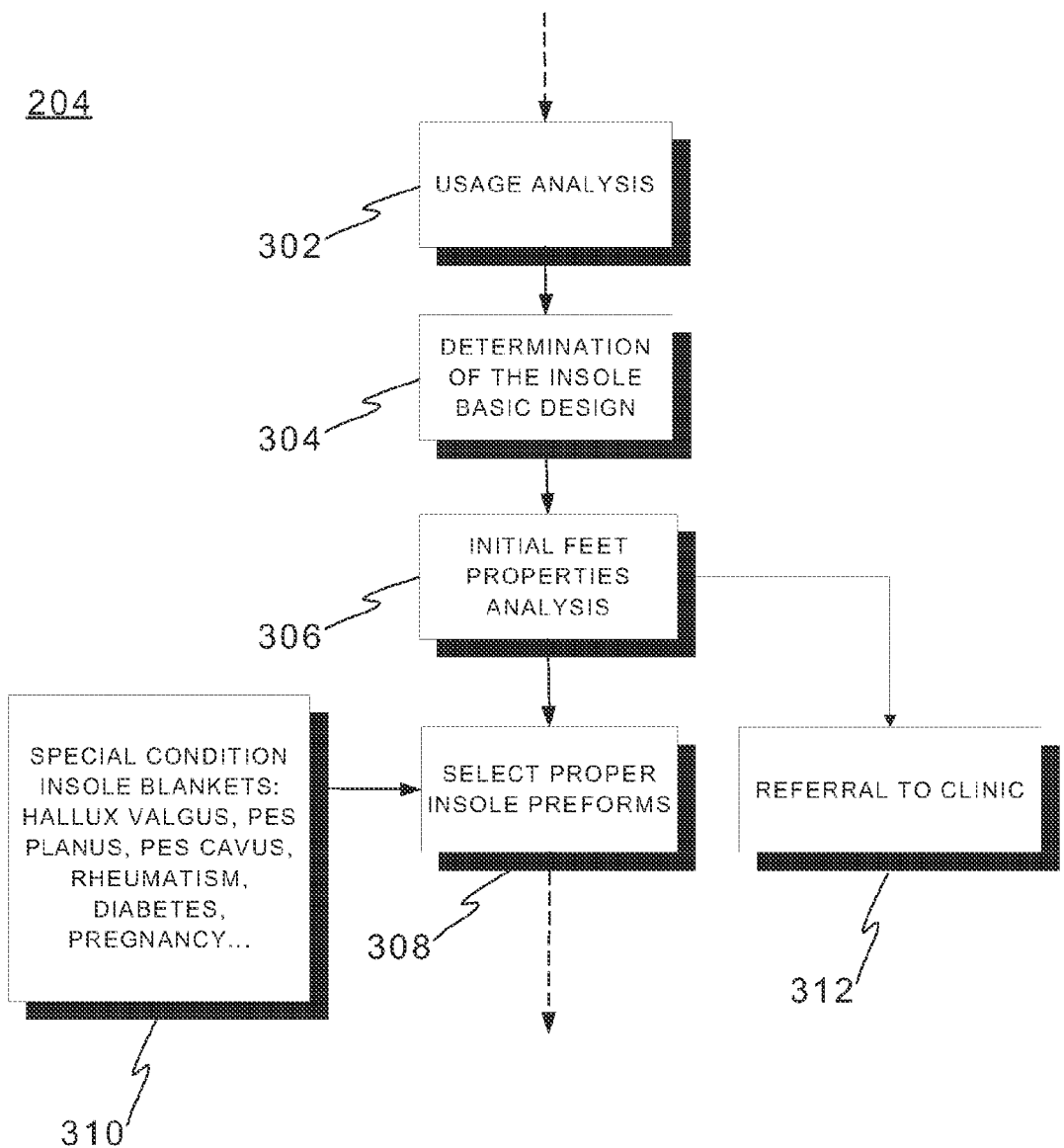
FIG. 3 is a more specific flow diagram about relevant analysis steps for determining the client's needs.
Figure 4:
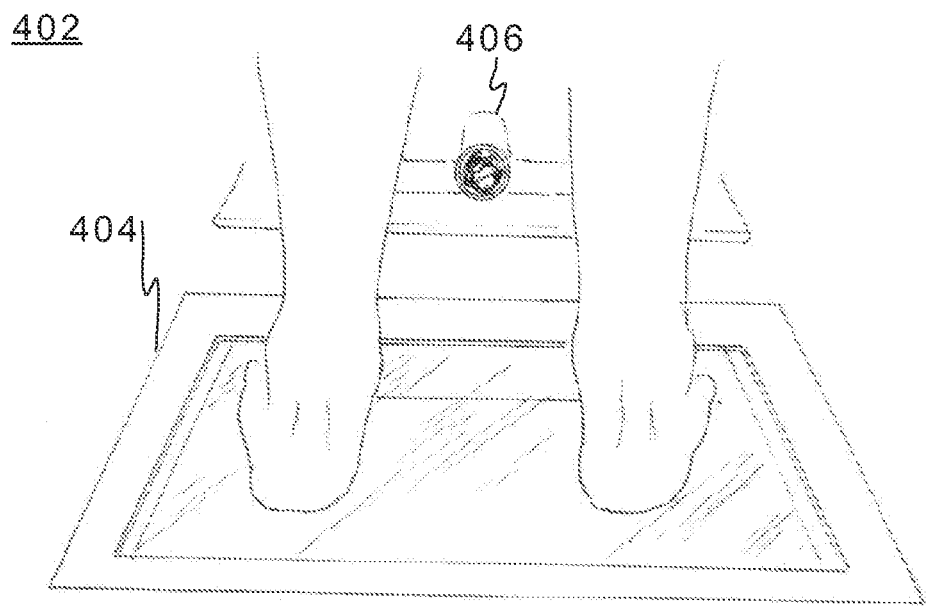
FIG. 4 depicts a podoscope including a transparent glass plate on which the client is standing during the feet analysis.
Figure 4:
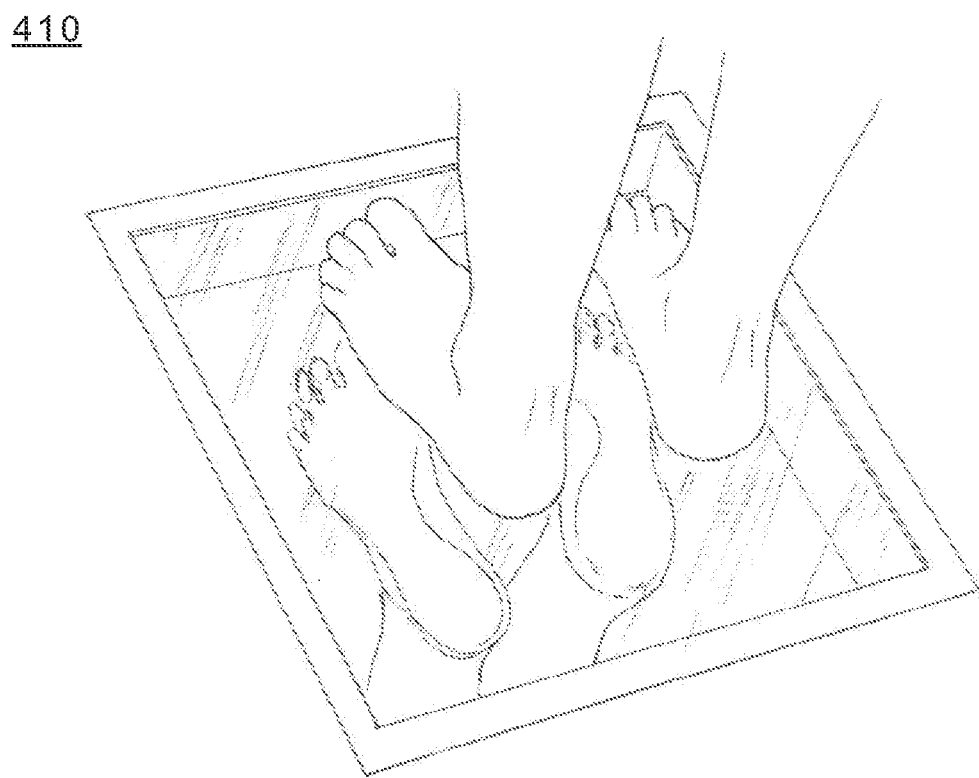

The analysis step 204 has been further illustrated in FIG. 3 to set forth different aspects included therein; first of all, a proper basic design or "style" of the insole may be determined 304, via usage analysis 302, from multiple options such as men's/women's, sport (general and optionally discipline-resolution such as tennis, running, soccer, football, basketball, hockey, skating, skiing, trekking, etc), health, military, medical and basic design, the design then affecting e.g. shape, material, thickness, elasticity, etc of the preform. The information for the analysis and decision-making (e.g. desired use/purpose of the insoles 302) may be gathered directly from the client by inquiring and monitoring his or her needs. The client may have brought along a pair of shoes to be used with the insoles, for example, which facilitates selecting a proper preform design and size.

In addition to mere basic design selection that heavily depends on the desired use, more refined data about the client's feet and their position (overpronation, oversupination, etc) may be collected 306 and reviewed via e.g. visual inspection and the study means such as the podoscope explained hereinbefore. A foot size is naturally a typical parameter/criterion required for determining a proper insole preform 308, although an oversized preform may in some applications be decently cut to a smaller size. The client may directly tell the size to the clerk, but the size may also be verified on the spot by utilizing available measurement equipment. Moreover, special conditions 310 such as hallux valgus, pes planus, pes cavus, rheumatism, diabetes, or pregnancy may imply a need for special preforms that are advantageously in the retailer stock as well. Rare situations may still occur wherein a responsible sales clerk notices that the client's feet and/or indicated use of the insoles require deeper investigation and a proper insole cannot be reliably addressed on the basis of the acquired information, or that the needed preforms are simply not available. The sales clerk may then refer the client to a specialized clinic employing foot specialists, e.g. physiotherapists or podiatrists, with more profound knowledge 312. Alternatively, the clerk may himself contact the clinic specialists for consultation and optionally order special preforms to the client, if possible. In the clinic more detailed examination shall be conducted; for example, neuromuscular, circulation joints, and soft tissues palpation and motion tests can be performed. The biomechanics of the lower extremities and the spine can be evaluated by videotaping the client's standing position, walking and running. Radiographs, bone scans, CT, MR, or sonography may also be available. Thus, by co-operation between the clinic and retail stores providing the insoles the client may receive fully guaranteed service, whereupon basic cases can be solved on the spot at retailer premises whereas more comprehensive study shall be carried out at the clinic.

Instead of verbally communicating with the client from the scratch, e.g. a computer with tailored software may be provided to interview the client about feet properties and intended use of the insoles, which then at least semi-automatically forms a client profile based on a predetermined set of profiling rules. Alternatively, the client may have his preferences already stored at the retailer due to an existing customer history, in which case the analysis step may be basically omitted provided his or her personal data and future use of the new insoles will substantially remain unchanged.

Anyway, the software or the sales clerk optionally assisted by the software may recommend a proper insole design to the client based on the available information, and a corresponding insole preform will be then picked up, preferably from the nearby rack where the preforms (or packages, each comprising one or two preforms) reside on view as conveniently grouped based on the sizes/designs thereof. As human feet are practically never of equal size or shape, the preforms may have been packed separately instead of traditional pair-packs. Alternatively, if the client already knows his needs without motivation for re-analysing the case, he may pick up proper preforms by himself after which he consults the clerk for the rest of the customisation procedure.

In step 206 a proper pair of preforms has already been determined and they are heated up to a temperature that enables reformation of at least predefined portions thereof as a response to a physical force introduced on them. The material selections for the preforms as explained hereinbefore guarantee a softening temperature for the predetermined portions that is still tolerable by the client, e.g. 85° C. After heating the preform to a reasonably high temperature as aforesaid 85° C., it is preferable to wait until the temperature drops to a more convenient reading like 70-75° C. from the standpoint of the client. Alternatively, the client may wear a sock or corresponding protection to insulate the foot from extensive heat. The heating device is advantageously selected and configured so that the heating up time is preferably only a few minutes or less in order to provide the client with swift service.

In step 208 the heated preforms are preferably placed on a flexible material like a casting pad (e.g. a pillow/cushion) of a molding stand, for example, and the client is instructed to introduce force via his soles to the preform surfaces meanwhile the clerk guides the client's feet to a proper position and manually, shapes, by physical interaction, e.g. through fingertips, the insoles to conform to the feet and achieve an improved mold according to the principles of the invention, see step 210 in FIG. 2 and numeral 506 in FIG. 5. Shaping may refer to introducing protrusions to a desired direction from the original insole form/plane, for example. Furthermore, the client may stand on the preforms to introduce the necessary pressure corresponding to the real weight bearing posture. Advantageously the molding stand includes a lower portion to receive one or more casting pads and the client's feet on top of those, and an upper portion such as a crossbar from which the client can seek support during the casting process.

In step 212 the clerk checks whether each insole conforms to the respective foot (sole) of the client and provides improved foot position and body posture, refer to numerals 508 and 510 of FIG. 5. In case there is still some tweaking to do, the method may be redirected to a proper antecedent step such as step 206, 208, or 210. Otherwise, the individually formed insoles are fit to the client's shoes, which may require slight further adjustments like cutting the border areas, etc 224.

The method execution is ended in step 216. It is waited until the temperature of the insoles drops under the glass transition temperature of the thermoplastic after which the insoles can be taken into use. In case the retailer in question is willing to maintain a customer register or forward such information to a centralized register possibly maintained by the retail chain, the insole manufacturer or some other third party, the customer data may be stored 226 to facilitate future business with the same client. This preferably happens only after receiving an explicit acceptance for storing personal information by the client. Step 226 may also include providing insole maintenance instructions to the client.

As an additional service, the clerks may be advised to channel the client's interest into the insoles of the invention even in the case the client is initially short of new shoes 222 only. This may happen either unconditionally or not until noticing a foot problem that the custom insole could alleviate.

The retail store may also offer a product guarantee that enables the client to get the preforms reshaped again by the retailer without any additional cost or with just a basic service fee, if a need arises.

Although the above method was described from the standpoint of a pair of insoles that are individually shaped to the client, which still is the preferred scenario, it is feasible for providing a single insole (or a single shoe) alike.

In the current invention also a liner or other element/layer to be placed in a shoe and possibly provided with a shoe or other footwear can be considered as the insole of the invention provided that it features similar effects and overall applicability.

Likewise, a shoe of the invention may be offered in the spirit of the above method. Especially a shoe sole or a part thereof may be constructed by following the ideas presented hereinbefore with reference to an insole. E.g. the sole of a soft gym shoe, a ballet shoe, a sandal or other type of shoe with soft enough portions suitable for manual molding after heating can be reformed accordingly.

It's clear to a skilled person that certain method steps can be also executed in reverse order, e.g. feet properties analysis 306 and an aggregate of usage analysis 302 and insole basic design selection 304; both aspects contribute to selecting a proper insole blanket 308.

Instead of heating, the preforms may be reshaped by utilizing some other feature than an embedded thermoplastic material. For example, certain resins can be hardened by utilizing predetermined chemical substances. However, in applying those it's important to select materials that enable trouble-free but still real-time reshaping of the preform on the client's foot, i.e. they must not introduce health hazards, e.g. burns, to the client upon or after the reshaping procedure.

In addition to humans, the invention may also be applied in manufacturing customized footwear for animals.

What is claimed is:

1. A method of producing an individually formed insole, comprising the steps of:
   providing an insole preform that comprises
      at least one layer made of thermoplastic material of one of the following: ABS, PVC, A-PET and PETG, said thermoplastic material becoming plastic above its glass transition temperature, which is substantially under 95° C. and above 45° C., wherein the at least one layer of thermoplastic material is configured to reach out from under a heel of a foot only to the metatarsophalangeal joint of the foot, and
   a lower layer configured to be placed against the footwear, wherein the lower layer is configured to reach from under the heel to the metatarsophalangeal joint and extend further to a toe of the foot;
   heating the preform above the glass transition temperature of the thermoplastic layer in case the preform lacks preheating;
   guiding the client to step on the heated preform;
   adjusting the client's foot so that the plantar arch settles to a normal high position;
   adjusting the angle of the ankle to the right position; and
   waiting for the temperature of the heated insole preform to drop under the glass transition temperature of the thermoplastic.

2. The method of claim 1 further comprising one or more of following steps:
   placing the insole preform on a soft pad;
   ensuring that the insole preform is following tightly the plantar arch and the foot is in correct position; and/or
   finish the shape of the insole to fit the inside dimensions of the shoe.

3. The method of claim 1, wherein the foot adjusting step comprises at least one of the following:
   pulling the client's toe up so that the plantar arch settles to a normal high position, and/or
   lifting the client's heel up while keeping the toes against a support surface.

4. A method of producing an individually formed shoe, comprising the steps of:
   providing a shoe preform that comprises
      a sole having at least two layers, a first of said two layers being made of thermoplastic material of one of the following: ABS, PVC, A-PET and PETG, said thermoplastic material becoming plastic above its glass transition temperature, which is substantially under 95° C. and above 45° C., wherein the first layer is configured to reach out from under a heel of a foot only to the metatarsophalangeal joint of the foot, and
      a second layer is configured to reach from under the heel to the metatarsophalangeal joint and extend further to a toe of the foot;
   heating the shoe preform above the glass transition temperature of the thermoplastic layer of the shoe preform in case the preforms lack preheating;
   guiding the client to step into the heated shoe preform;
   adjusting the client's foot so that the plantar arch settles to a normal high position;
   adjusting the angle of the ankle to the right position;
   taking the shoe preform off from the foot; and
   waiting for the temperature of the heated shoe preform to drop under the glass transition temperature of the thermoplastic.

5. The method of claim 4 wherein the method further comprises one or more of following steps:
   placing the shoe preform on a soft pad; and
   ensuring that the shoe preform is following tightly the plantar arch and the foot is in correct position.

6. The method of claim 4, wherein the foot adjusting step comprises at least one of the following:
   pulling the client's toe up so that the plantar arch settles to a normal high position; and/or
   lifting the client's heel up while keeping the toes against a support surface.

* * * * *